United States Patent [19]

Harris, Jr.

[11] 4,391,966

[45] * Jul. 5, 1983

[54] POLYMERS FROM PHENYLTEREPHTHALIC ACID

[75] Inventor: John F. Harris, Jr., Wilmington, Del.

[73] Assignee: E. I. Du Pont de Nemours and Company, Wilmington, Del.

[*] Notice: The portion of the term of this patent subsequent to Oct. 13, 1998, has been disclaimed.

[21] Appl. No.: 286,559

[22] Filed: Jul. 24, 1981

Related U.S. Application Data

[63] Continuation-in-part of Ser. No. 102,040, Dec. 10, 1979, Pat. No. 4,294,955.

[51] Int. Cl.³ .............................................. C08G 63/18
[52] U.S. Cl. ................... 528/176; 264/176 F; 528/190; 528/193; 528/194
[58] Field of Search ................ 528/176, 190, 193, 194

[56] References Cited

U.S. PATENT DOCUMENTS

| | | | |
|---|---|---|---|
| 3,160,603 | 12/1964 | Holub | 528/191 |
| 3,723,388 | 3/1973 | Bell et al. | 528/193 |
| 4,065,432 | 12/1977 | Frazer | 264/176 F X |
| 4,118,372 | 10/1978 | Schaefzen | 528/191 |
| 4,153,779 | 5/1979 | Jackson, Jr. et al. | 528/193 |
| 4,156,070 | 5/1979 | Jackson, Jr. et al. | 528/191 X |
| 4,159,365 | 6/1979 | Payet | 528/176 X |
| 4,183,895 | 1/1980 | Luise | 528/191 |
| 4,287,332 | 9/1981 | Jackson et al. | 528/176 |
| 4,294,955 | 10/1981 | Harris, Jr. | 528/176 |
| 4,299,756 | 11/1981 | Calundann | 528/176 X |

FOREIGN PATENT DOCUMENTS 885739 12/1961 United Kingdom .
993272 5/1965 United Kingdom .

OTHER PUBLICATIONS

Chem. Abstracts, vol. 49, (1954), 5396g, from Annalen 586, 138–146, (1954).
PCT International Publication No. WO79/01034, Application No. PCT/US/79/00289, Published Nov. 29, 1979.

Primary Examiner—Howard E. Schain

[57] ABSTRACT

Melt-spinnable, anisotropic melt-forming aromatic polyesters prepared from phenylterephthalic acid or mixtures thereof with terephthalic acid, one or more selected aromatic diols, and 4-hydroxybenzoic acid; and filaments of such polyesters, the tenacity of which filaments can be increased by heat treatment.

9 Claims, No Drawings

POLYMERS FROM PHENYLTEREPHTHALIC ACID

This is a continuation-in-part of application Ser. No. 102,040 filed Dec. 10, 1979 and issued Oct. 13, 1981 as U.S. Pat. No. 4,294,955.

TECHNICAL FIELD

This invention relates to fiber-forming, melt-spinnable aromatic polyesters and to filaments therefrom.

BACKGROUND

Melt-spinnable, aromatic polyesters prepared from aromatic diols and mono-substituted terephthalic acids wherein the substituents include Br, Cl, alkyl of 1–3 carbon atoms and alkoxyl are known (U.S. Pat. Nos. 4,065,432; 4,156,070; U.K. Pat. No. 993,272). Polyesters containing phenyl-substituted isophthalic acid are disclosed in U.K. Pat. No. 885,739.

Melt-spinnable, fiber-forming polyesters capable of forming optically anisotropic melts, prepared from monophenylhydroquinone and terephthalic acid, are disclosed in U.S. Pat. No. 4,159,365.

Phenylterephthalic acid is known (Annalen 586, 138–46 (1954)).

The art is confusing on the relative effects of substituents on the diacid and diol components of aromatic polyesters. U.S. Pat. No. 4,118,372 teaches that, in the preparation of aromatic, melt-spinnable polyesters capable of forming optically anisotropic melts, it is preferable that the diol be substituted with halogen or lower alkyl and that the diacid remain unsubstituted because of thermal or hydrolytic instability and/or cost of copolymers prepared from ring-substituted aromatic diacids. U.S. Pat. No. 3,160,603 teaches that aromatic, fiber-forming, initially amorphous polyesters in which the diacid is chloro-substituted show much less tendency to crystallize than isomeric polyesters wherein the diol is chloro-substituted. U.K. Pat. No. 993,272 discloses unexpectedly crystalline polyesters prepared from (asymmetric) monoethyl-, alkoxyl- or chloro-substituted terephthalic acid and like-substituted hydroquinone. A substantial amount of an unsubstituted third reactant (diacid or diol) may be incorporated while retaining crystallinity.

U.S. Pat. No. 4,118,372, supra, also discloses aromatic melt-spinnable copolyesters, capable of forming optically anisotropic melts, which contain recurring units of $(O-R_1-O)$, $(OC-R_2-CO)$, and $(O-R_3-CO)$ wherein $R_1$, $R_2$, and $R_3$ are arylene radicals, including 1,4-phenylene, 4,4'-biphenylene and 2,6-naphthylene, and $R_1$ and $R_3$ can contain one or more substituents, including lower alkyl of 1–4 carbon atoms.

U.S. Pat. No. 4,159,365, supra, also discloses that polyesters containing units derived from monophenylhydroquinone and terephthalic acid may also contain units derived from 4-hydroxybenzoic acid, 4,4'-dihydroxybiphenyl and 1,4-hydroquinone.

U.S. Pat. No. 4,242,496 and the related PCT Application Publication Number WO79/01034 disclose melt-spinnable, aromatic, liquid crystal (anisotropic melt) copolyesters of terephthalic acid, phenylhydroquinone and p-hydroxybenzoic acid (HBA). The polyesters contain 25 to 80 mole percent HBA, based on total moles of diacid and hydroxy acid, and exhibit melting points which decrease with increasing HBA content, the melting point reaching a minimum at about 20 mole percent HBA, then rising again with increasing HBA content. Minimum softening temperatures occur at 60 to 70 mole percent HBA.

SUMMARY OF THE INVENTION

This invention provides melt-spinnable, fiber-forming polyesters that are optically anisotropic in the melt and which consist essentially of recurring units having the structural formulas (1) (a) 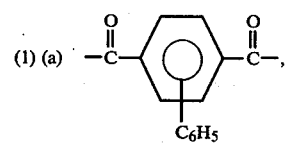

or a combination of (a) and up to 50 mole percent of (b) 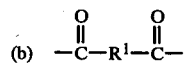

wherein $R^1$ is 1,4-phenylene, 2,6-naphthylene, 4,4'-biphenylene, or a mixture of any thereof;

(2) (a) $-O-R^2-O-$ wherein $R^2$ is 1,4-phenylene, monochloro-, monophenyl-, or monoalkyl-1,4-phenylene wherein alkyl contains 1 to 4 carbon atoms, 2,6-naphthylene, 1,4-naphthylene, 4,4'-biphenylene or a mixture of any thereof, or a combination of (a) and up to 20 mole percent of (b) 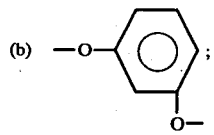

and (3) based on the total moles of (1) and (3), 25 to 80 mole percent, preferably 30 to 70 mole percent, of

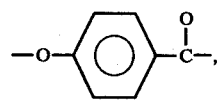

the recurring diacid units (1) and recurring dioxy units (2) being present in substantially equimolar amounts.

The polyesters of this invention may be prepared by standard melt-polymerization techniques from the appropriate aromatic dicarboxylic acids, aromatic diols, and 4-hydroxybenzoic acid (HBA) that provide the units described above. Thus, phenylterephthalic acid may be employed as the sole acid reactant or it may be combined with one or more diacids selected from the group consisting of terephthalic acid, 2,6-naphthalene dicarboxylic acid and 4,4'-bibenzoic acid, in such amounts that the phenylterephthalic acid constitutes at least 50 mole percent of the acid mixture. The diol reactant(s) is selected from the group consisting of hydroquinone, monochloro-, monophenyl-, or monoalkylhydroquinone wherein alkyl contains 1 to 4 carbon atoms, 1,4-dihydroxynaphthalene, 2,6-dihydroxynaphthalene, and 4,4'-dihydroxybiphenyl. Resorcinol may be employed in addition to one or more of the aforementioned diols in an amount of up to 20 mole percent based on the total moles of diol reactant. It is ordinarily preferred to employ the diols in the form of diesters because said esters can usually be prepared in high purity, of importance in the preparation of high molecular weight polyesters. It also is preferable to employ HBA in the form of a 4-acyloxybenzoic acid ester for the same reason.

Diols or diesters, preferably diesters, most preferably diacetates, and diacids are normally combined, in substantially equimolar amounts, with the aforesaid 25 to 80 mole percent of HBA or, preferably, its acyloxyester, most preferably its acetoxyester, and heated in a stirred reaction vessel in an inert atmosphere, e.g., under nitrogen or in vacuum, with stirring for about 30 minutes to 36 hours. A stoichiometric excess of either diacid or diol (diester) of up to 10 mole percent may be used without detriment. Temperatures employed for the polymerization are above the melting points of the reactants and are generally in the range of about 200° to about 350° C. The reaction vessel is equipped with a means to permit by-product removal during polymerization; for example, a combined distillation head-condenser.

Reaction is generally initiated at about 250° to 290° C. and the temperature is gradually raised in stages as polymerization proceeds. Towards the end of the polymerization, the molten polymer may be placed under reduced pressure and heated further to complete the by-product removal and the polymerization. Optionally, the molten polymer may be transferred directly to an appropriate apparatus for preparation of shaped articles, e.g., a fiber spinning unit. Polymerization conditions such as temperature, duration of heating, pressures and the like, may be varied according to the reactants employed and the degree of polymerization desired.

In an alternative, but less preferred, procedure, the diacids, diols, and HBA may be employed in the form of diesters. In such cases a catalyst such as dibutyl tin oxide may be desirable.

DETAILED DESCRIPTION OF THE INVENTION

The polyesters of this invention have molecular weights and melting points sufficient for melt-spinning into filaments.

A preferred polyester composition of this invention, having recurring units of the formula

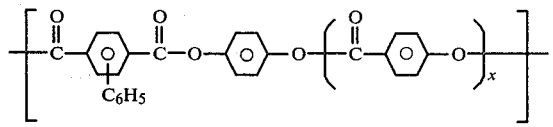

wherein x is 0.33 to 4, prepared from phenylterephthalic acid, hydroquinone, and HBA, differs from a prior art polyester disclosed in U.S. Pat. No. 4,242,496 wherein the phenyl substituent is located on the diol segment, i.e.,

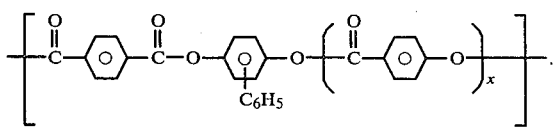

As is shown in Example 1, the polymer of this invention, surprisingly, is significantly lower melting than such art polymers of the same HBA content. Accordingly, the polyesters of this invention can tolerate higher levels of HBA, a relatively low-cost monomer, than the similar art polyesters while remaining melt-processible at commercially acceptable temperatures, a significant economic advantage.

FILAMENT PREPARATION

The preferred polyesters of this invention may be spun into filaments by conventional melt-spinning techniques. A melt of the polymer is extruded through a spinneret into a quenching atmosphere (e.g., air or nitrogen maintained at room temperature) and wound up. General spinning conditions are given in U.S. Pat. No. 4,066,620.

As used herein, the term "as-spun" fiber refers to a fiber which has not been drawn or heat treated after extrusion and normal windup.

HEAT TREATMENT AND UTILITY

The as-spun fibers of this invention may be subjected to heat treatment in an oven while relaxed to provide high strength fibers useful for a variety of industrial applications such as plastic and rubber reinforcement. In the heat treating process, fiber samples, as skeins or on bobbins (preferably collapsible bobbins) are usually heated in an inert atmosphere that is continuously purged by flow of inert gas such as nitrogen through the oven to remove by-products from the vicinity of the fiber. Temperatures approaching the fusion point but sufficiently below to prevent interfilament fusion are employed. Preferably the maximum temperature is reached in a stepwise or gradual fashion.

MEASUREMENTS AND TESTS

Inherent Viscosity ($\eta_{inh}$) is defined by the equation $$\eta_{inh} = \frac{\ln(\eta_{rel})}{C}$$

wherein ($\eta_{rel}$) represents the relative viscosity and C represents a concentration of 0.25 gram of the polymer in 100 ml of solvent. The relative viscosity ($\eta_{rel}$) is determined by dividing the flow time in a capillary viscometer of the dilute solution by the flow time for the pure solvent. Flow times are determined at 25° C., and the solvent is 1:1 hexafluoroisopropanol/chloroform unless otherwise indicated.

Fiber tensile properties are reported in conventional units as follows (conversion factors for SI units are given in parentheses):

| | |
|---|---|
| Denier | in g/9000m (1.11 dtex) |
| Tensile Strength (Tenacity) | in g/denier (0.89 dN/tex) |
| Elongation | in percent of unstretched length |
| Initial Modulus | in g/denier (0.89 dN/tex) |

They are measured using the procedures shown in Morgan U.S. Pat. No. 3,827,998 on fibers that have been conditioned for at least one hour. At least three breaks are averaged.

The Thermooptical Test (TOT), which involves heating a polymer sample between crossed (90°) polarizers on the heating stage of a polarizing microscope, is fully described in U.S. Pat. No. 4,066,620. Polymers that pass this test (+) are considered to be optically anisotropic in the molten state.

The melting behavior and fiber-forming capability of polyesters of this invention were determined by heating a sample of the polymer on a metal block, as described in the ensuing examples which are illustrative of the present invention. The polymer flow temperature was determined on the hot stage polarizing microscope.

The term "consisting essentially of" is intended to have its customary meaning, namely, that all specified materials and conditions are very important in practicing the invention but that unspecified materials and conditions are not excluded so long as they do not prevent the benefits of the invention from being realized.

In the following examples all temperatures are in degrees Celcius unless otherwise indicated.

EXAMPLE 1

A. Copolyester of Phenylterephthalic Acid, Hydroquinone, and HBA, Containing 0.5 Mole of HBA per Mole of Phenylterephthalic Acid All equipment was dried in an oven at 135° and allowed to cool in a nitrogen atmosphere. In a 200 ml flask was placed 3.72 g of 4-acetoxybenzoic acid, 10.00 g of phenylterephthalic acid and 8.02 g of hydroquinone diacetate. The flask was fitted with a 15 cm extension tube and a short path still head which had a small paddle stirrer instead into it reaching to the bottom of the reactor and a small round-bottomed flask as receiver. The assembled set-up was connected to a nitrogen bubbler, and then the mixture was heated in an oil bath, stirred, and evacuated according to the following schedule:
Oil Bath Temperature
225°–226°: 1 h 48 min, stirred 43 min
224°–250°: 1 h 5 min
250°–256°: 30 min
256°–245°: 18 h 20 min
245°–280°: 1 h 12 min
280°: 7 h 34 min (0.05–0.10 mm) stirred 14 min The reactor was allowed to cool under vacuum and 13.2 g of polymer was isolated. After being ground in a Wiley mill sufficient to pass through a 40 mesh screen (U.S. Sieve Series), the polymer was dried at 200° for about 16 h in a vacuum oven. Inherent viscosity was 3.97. The polyester, when heated between crossed polarizers on a hot stage microscope, flowed at 337°. TOT was positive.

This polyester was melt-spun at 338°–365° to give filament. Filament that was collected at 338° had the following properties:
Tensile Strength: 1.56 g/denier
% Elongation: 0.48%
Initial Modulus: 249 g/d A sample of this filament was heated in a nitrogen atmosphere according to the following schedule:
Rm. Temp. −160°: few minutes
160°–200°: 2 h
200°–310°: 5.5 h
310°: 14 h
310°–Rm. Temp.: about 2 h After this heat treatment values of tensile strength and initial modulus up to 7.92 g/denier and 299 g/denier, respectively, were obtained.

B. Copolyester of Phenylterephthalic Acid, Hydroquinone, and HBA, Containing 1.0 Mole of HBA per Mole of Phenylterephthalic Acid Using the procedure described in Part A, a mixture of 7.44 g of 4-acetoxybenzoic acid, 10.00 g of phenylterephthalic acid and 8.02 g of hydroquinone diacetate was heated in an oil bath, stirred and evacuated according to the following schedule:
Oil Bath Temperature
230°–221°: 51 min
221°–220°: 36 min, stirred
220°–250°: 1 h 14 min
250°: 18 h 52 min
250°–273°: 46 min
273°–300°: 7 h 38 min (0.10 mm)

The product was isolated and worked up as described in Part A; 15.5 g of polymer was obtained having an inherent viscosity of 3.68. This polyester, when heated between crossed polarizers on a hot stage microscope, flowed at 357°. TOT was positive.

Melt-spinning of this polyester at 369°–375° give filament. Filament that was collected at 369° had the following properties:
Tensile Strength: 4.76 g/denier
% Elongation: 1.45%
Initial Modulus: 320 g/denier A sample of this filament was heated in a nitrogen atmosphere according to the following schedule:
150°–280°: 6.8 h
280°: 9 h
280°–150°: 7.5 h After this heat treatment, values of tensile strength and initial modulus up to 8.27 g/denier and 530 g/denier, respectively, were obtained.

C. Copolymer of Phenylterephthalic Acid, Hydroquinone, and HBA, Containing 1.21 Moles of HBA per Mole of Phenylterephthalic Acid Using the procedure described in Part A, a mixture of 9.01 g of 4-acetoxybenzoic acid, 10.00 g of phenylterephthalic acid, and 8.02 g of hydroquinone diacetate was heated in an oil bath, stirred, and evacuated according to the following schedule:
Oil Bath Temperature
225°–221°: 2 h 4 min, stirred 37 min
221°–250°: 30 min
250°–243°: 18.75 h
243°–268°: 12 min
268°–273°: 2 h 3 min
273°–274°: 5.75 h (0.05–0.10 mm)

The product was isolated and worked up as described in Part A; 15.4 g of polymer was obtained having an inherent viscosity of 2.55. This polyester, when heated between crossed polarizers on a hot stage microscope, flowed at 265°. TOT was positive.

Melt-spinning of this polyester at 337° gave filament that had the following properties:
Tensile Strength: 3.66 g/denier
% Elongation: 1.10%
Initial Modulus: 328 g/denier A sample of this filament was heated in a nitrogen atmosphere according to the following schedule:
155°–288°: 6.8 h
288°: 9 h
288°–125°: 8.75 h After this heat treatment, values of tensile strength and initial modulus up to 9.49 g/denier and 383 g/denier, respectively, were obtained.

D. Copolyester of Phenylterephthalic Acid, Hydroquinone, and HBA, Containing 2.63 Moles of HBA per Mole of Phenylterephthalic Acid Using the procedure described in Part A, a mixture of 13.71 g of 4-acetoxybenzoic acid, 7.00 g of phenylterephthalic acid and 5.61 g of hydroquinone diacetate was heated in an oil bath, stirred and evacuated according to the following schedule:

Oil Bath Temperature
224°–230°: 1 h 53 min, stirred 40 min
230°–247°: 28 min
247°–244°: 18 h 27 min
244°–300°–280°: 2.25 h
280°–276°: 5 h 40 min (0.05–0.10 mm)

The product was isolated and worked up as described in Part A; 15.34 g of polymer was obtained having an inherent viscosity of 3.36. This polyester, when heated between crossed polarizers on a hot stage microscope, flowed at 345°. TOT was positive.

E. Comparison of Phenylterephthalic Acid/Hydroquinone/HBA Polyesters and Terephthalic Acid/Phenylhydroquinone/HBA Polyesters The polyesters (I) of Parts A–D were compared in melting points and softening temperatures with isomeric polyesters (II) having the phenyl substituent on the diol instead of the diacid.

The isomeric polyesters (II) were prepared by substantially the same procedures used in Parts A–D except that terephthalic acid and phenylhydroquinone diacetate were used in place of phenylterephthalic acid and hydroquinone diacetate, respectively, in the following amounts:

| Isomer to Polyester of Part | Terephthalic Acid (g) | Phenylhydroquinone Diacetate (g) |
|---|---|---|
| A | 6.86 | 11.16 |
| B | 6.86 | 11.16 |
| C | 6.86 | 11.16 |
| D | 4.80 | 7.81 |

The eight isomeric polyesters thus prepared were compared at four levels of HBA content, that is, at four different mole percentages of p-acetoxybenzoic acid, based on the total moles of p-acetoxybenzoic acid and diacid present. The four levels are reflected in the following comparison table.

Melting points (MP) were determined by differential scanning calorimetry. Softening temperatures (ST) were determined with a Du Pont 941 Thermomechanical Analyzer, using a 10 g weight on a 0.025 in (0.6 mm) diameter tipped probe and a scan rate of 10°/min. Inherent viscosity was measured in 1:1 hexafluoroisopropanol/chloroform at 25° using 0.25 g of polymer per 100 ml of solvent.

| p-Acetoxybenzoic Acid (mole %) | Polyester I | | | Polyester II | | |
|---|---|---|---|---|---|---|
| | inh | ST (°C.) | MP (°C.) | inh | ST (°C.) | MP (°C.) |
| 33 | 3.97 | 160 | 288 | 2.76 | 165 | 330 |
| 50 | 3.68 | 125 | 320 | 3.20 | 165 | 369 |
| 55 | 2.55 | 145 | 330 | 4.16 | 185 | 389 |
| 72 | 3.36 | 140 | 391 | 4.45 | 180 | 437 |

The comparisons show that polyesters from phenylterephthalic acid, hydroquinone and HBA melt and soften at significantly lower temperatures than polyesters from terephthalic acid, phenylhydroquinone and an equivalent amount of HBA.

EXAMPLE 2

A. Copolyester of Phenylterephthalic Acid, Methylhydroquinone, and HBA, Containing 1.0 Mole of HBA per Mole of Phenylterephthalic Acid Using the procedure described in Example 1A, a mixture of 8.92 g of 4-acetoxybenzoic acid, 12.00 g of phenylterephthalic acid and 10.83 g of methylhydroquinone diacetate was heated in an oil bath, stirred, and evacuated according to the following schedule:

Oil Bath Temperature
280°: 4 min
280°–285°: 32 min, stirred
285°: 1 h 39 min
285°: 2 h (0.05 mm)
285°–325°: 5 min (0.05 mm)
325°: 20 min (0.05 mm)

The product was isolated and worked up as described in Example 1A except that the ground polymer was passed through a 20 mesh screen (U.S. Sieve Series); 16.20 g of polymer was obtained having an inherent viscosity of 2.81. This polyester formed an anisotropic melt above its flow temperature of 279°.

Melt-spinning of this polyester at 330° gave filament with the following properties:
Tensile Strength: 4.52 g/denier
% Elongation: 1.45%
Initial Modulus: 365 g/denier B. Copolyester of Phenylterephthalic Acid, Methylhydroquinone, and HBA, Containing 2.0 Moles of HBA per Mole of Phenylterephthalic Acid Using the procedure described in Example 1A, a mixture of 14.87 g of 4-acetoxybenzoic acid, 10.00 g of phenylterephthalic acid, and 9.03 g of methylhydroquinone diacetate was heated in an oil bath, stirred, and evacuated according to the following schedule:

Oil Bath Temperature
280°: 7 min
280°–284°: 1 h 58 min, stirred
284°–300°: 5 min, stirred
300°–302°: 62 min, stirred
302°–325°: 3 min, stirred
325°: 7 min
325°: 33 min (0.10–0.20 mm)

The product was isolated and worked up as described in Part A; 21.2 g of polymer was obtained having an inherent viscosity of 2.12.

Melt-spinning of this polyester at 325°–338° gave lustrous filament. Filament collected at 338° had the following properties:
Tensile Strength: 4.05 g/denier
% Elongation: 1.53%
Initial Modulus: 248 g/denier

EXAMPLE 3

A. Copolyester of Phenylterephthalic Acid, Phenylhydroquinone, and HBA, Containing 1.0 Mole of HBA per Mole of Phenylterephthalic Acid Using the procedure described in Example 1A, a mixture of 10.00 g of 4-acetoxybenzoic acid, 13.45 g of phenylterephthalic acid, and 15.75 g of phenylhydroquinone diacetate was heated in an oil bath, stirred, and evacuated according to the following schedule:

Oil Bath Temperature
280°–283°: 45 min, stirred 38 min
283°–280°: 1 h 17 min
280°–285°: 2 h 3 min (0.05–0.10 mm)
285°–325°: 3 min (0.05–0.10 mm)

325°: 30 min (0.05–0.10 mm)
The product was isolated and worked up as described in Example 2A; 24.5 g of polymer was obtained having an inherent viscosity of 1.54.

Melt-spinning of this polyester at 275°–297° yielded lustrous filament. Filament collected at 297° had the following properties:
Tensile Strength: 4.11 g/denier
% Elongation: 2.17%
Initial Modulus: 249 g/denier The product from another preparation of this copolymer, having an inherent viscosity of 2.75, was shown to be anisotropic above its flow temperature of 195°.

B. Copolyester of Phenylterephthalic Acid, Phenylhydroquinone, and HBA, Containing 2.0 Moles of HBA per Mole of Phenylterephthalic Acid Using the procedure described in Example 1A, a mixture of 13.33 g of 4-acetoxybenzoic acid, 8.96 g of phenylterephthalic acid, and 10.00 g of phenylhydroquinone diacetate was heated in an oil bath, stirred, and evacuated according to the following schedule:
Oil Bath Temperature
280°–286°: 35 min, stirred 31 min
286°–284°: 1 h 35 min
284°–282°: 2 h 5 min (0.05 mm)
282°–320°: 6 min (0.05 mm)
320°–325°: 17 min (0.05 mm)
The product was isolated, ground up in a micro mill, and dried in a vacuum oven at 190° for about 17 h; 18.9 g of polymer was obtained having an inherent viscosity of 3.69. This polyester formed an anisotropic melt above its flow temperature of 260°.

Melt-spinning of this polyester at 320° gave filament which had the following properties:
Tensile Strength: 5.45 g/denier
% Elongation: 1.53%
Initial Modulus: 376 g/denier C. Copolyester of Phenylterephthalic Acid, Phenylhydroquinone, and HBA, Containing 3.0 Moles of HBA per Mole of Phenylterephthalic Acid Using the procedure described in Example 1A, a mixture of 20.01 g of 4-acetoxybenzoic acid, 8.96 g of phenylterephthalic acid, and 10.00 g of phenylhydroquinone diacetate was heated in an oil bath, stirred, and evacuated according to the following schedule:
Oil Bath Temperature
286°–284°: 34 min, stirred 30 min
284°–280°: 1 h 41 min
280°–326°: 6 min
326°: 1 h (0.05 mm)
The product was isolated, ground up in a micro mill, and dried in a vacuum oven at 150° for about 17 h; 21.8 g of polymer was obtained having an inherent viscosity of 2.99. This polyester formed an anisotropic melt above its flow temperature of 289°.

Melt-spinning of this polyester at 348° gave filament that had the following properties:
Tensile Strength: 3.63 g/denier
% Elongation: 1.38%
Initial Modulus: 252 g/denier A sample of this filament was heated in a nitrogen atmosphere according to the following schedule:
160°–290°: 6.8 h
290°: 9 h
290°–160°: 6.5 h
After this heat treatment, values of tensile strength and initial modulus up to 6.89 g/denier and 294 g/denier, respectively, were obtained.

EXAMPLE 4

A. Copolyester of Phenylterephthalic Acid, 4,4'-Dihydroxybiphenyl, and HBA, Containing 1.0 Mole of HBA per Mole of Phenylterephthalic Acid Using the procedure described in Example 1A, a mixture of 8.92 g of 4-acetoxybenzoic acid, 12.00 g of phenylterephthalic acid, and 13.39 g of 4,4'-dihydroxybiphenyl diacetate was heated in an oil bath, stirred, and evacuated according to the following schedule:
Oil Bath Temperature
284°: 41 min, stirred 36 min
284°–280°: 1 h 49 min
280°–286°: 1 h (0.05–0.10 mm)
286°–325°: 11 min (0.05–0.10 mm)
325°: 25 min (0.05–0.10 mm)
The product was isolated and worked up as described in Example 1A; 20.6 g of polymer was obtained having an inherent viscosity of 2.40. This polyester formed an anisotropic melt above its flow temperature of 250°.

Melt-spinning of this polyester at 269°–300° gave lustrous filament. Filament collected at 300° had the following properties:
Tensile Strength: 4.53 g/denier
% Elongation: 1.87%
Initial Modulus: 347 g/denier A sample of this filament was heated in a nitrogen atmosphere according to the following schedule:
160°–280°: 6.8 h
280°: 9 h
280°–150°: 4 h
After this heat treatment, values of tensile strength and initial modulus up to 14.78 g/denier and 412 g/denier, respectively, were obtained.

B. Copolyester of Phenylterephthalic Acid, 4,4'-Dihydroxybiphenyl, and HBA, Containing 2.0 Moles of HBA per Mole of Phenylterephthalic Acid Using the procedure described in Example 1A, a mixture of 17.85 g of 4-acetoxybenzoic acid, 12.00 g of phenylterephthalic acid, and 13.39 g of 4,4'-dihydroxybiphenyl diacetate was heated in an oil bath, stirred, and evacuated according to the following schedule:
Oil Bath Temperature
280°–282°: 37 min, stirred 30 min
282°–280°: 1 h 40 min
280°–284°: 2 h 3 min (0.10 mm)
284°–328°: 5 min (0.10 mm)
328°–325°: 12 min (0.10 mm)
The product was isolated, ground up in a Wiley Mill, and dried in a vacuum oven at 190° for about 17 h; 24.9 g of polymer was obtained having an inherent viscosity of 3.56. This polyester formed an anisotropic melt above its flow temperature of 254°.

Melt-spinning of this polyester at 308°–335° gave lustrous filament. Filament collected at 335° had the following properties:
Tensile Strength: 4.42 g/denier
% Elongation: 1.58%
Initial Modulus: 382 g/denier A sample of this filament was heated in a nitrogen atmosphere according to the following schedule:
160°–270°: 6 h
270°: 10 h
270°–160°: 4 h
After this heat treatment, values of tensile strength and initial modulus up to 15.40 g/denier and 535 g/denier, respectively, were obtained.

C. Copolyester of Phenylterephthalic Acid, 4,4'-Dihydroxybiphenyl, and HBA, Containing 3.0 Moles of HBA per Mole of Phenylterephthalic Acid Using the procedure described in Example 1A, a mixture of 15.62 g of 4-acetoxybenzoic acid, 7.00 g of phenylterephthalic acid, and 7.81 g of 4,4'-dihydroxybiphenyl diacetate was heated in an oil bath, stirred, and evacuated according to the following schedule:
Oil Bath Temperature
280°–283°: 25 min, stirred 21 min
283°–285°: 45 min
285°–284°: 2 h (0.10 mm)
284°–325°: 5 min (0.10 mm)
325°: 15 min (0.10 mm)
The product was isolated, ground up in a micro mill to pass through a 20 mesh screen (U.S. Sieve Series), and dried in a vacuum oven at 190° for about 17 h; 18.9 g of polymer was obtained having an inherent viscosity of 2.69. This polyester formed an anisotropic melt above its flow temperature of 285°.

Melt-spinning of this polyester at 288°–317° gave lustrous filament. Filament collected at 317° had the following properties:
Tensile Strength: 4.34 g/denier
% Elongation: 1.19%
Initial Modulus: 365 g/denier
A sample of this filament was heated in a nitrogen atmosphere according to the following schedule:
160°–280°: 6.8 h
280°: 9 h
280°–160°: 4 h
After this heat treatment, values of tensile strength and initial modulus up to 12.99 g/denier and 585 g/denier, respectively, were obtained.

EXAMPLE 5

A. Copolyester of Phenylterephthalic Acid, 2,6-Dihydroxynaphthalene, and HBA, Containing 1.0 Mole of HBA per Mole of Phenylterephthalic Acid Using the procedure described in Example 1A, a mixture of 8.92 g of 4-acetoxybenzoic acid, 12.00 g of phenylterephthalic acid, and 12.83 g of 2,6-dihydroxynaphthalene diacetate was heated in an oil bath, stirred, and evacuated according to the following schedule:
Oil Bath Temperature
280°–290°: 37 min, stirred 29 min
290°–284°: 1 h 28 min
284°–286°: 2 h (0.05 mm)
286°–325°: 5 min (0.05 mm)
325°: 15 min (0.05 mm)
The product was isolated, ground up in a micro mill to pass through a 40 mesh screen (U.S. Sieve Series), and dried in a vacuum oven at 200° for about 17 h; 19.4 g of polymer was obtained having an inherent viscosity of 1.85. This polyester formed an anisotropic melt above its flow temperature of 208°.

Melt-spinning of this polyester at 279°–310° gave lustrous filament. Filament collected at 310° had the following properties:
Tensile Strength: 4.19 g/denier
% Elongation: 1.90%
Initial Modulus: 248 g/denier
A sample of this filament was heated in a nitrogen atmosphere according to the following schedule:
160°–270°: 6 h
270°: 10 h
270°–160°: 4 h After this heat treatment, values of tensile strength and initial modulus up to 10.47 g/denier and 294 g/denier, respectively, were obtained.

B. Copolyester of Phenylterephthalic Acid, 2,6-Dihydroxynaphthalene, and HBA, Containing 2.0 Moles of HBA per Mole of Phenylterephthalic Acid Using the procedure described in Example 1A, a mixture of 17.85 g of 4-acetoxybenzoic acid, 12.00 g of phenylterephthalic acid, and 12.83 g of 2,6-dihydroxynaphthalene diacetate was heated in an oil bath, stirred, and evacuated according to the following schedule:
Oil Bath Temperature
280°–284°: 39 min, stirred 33 min
284°–280°: 1 h 33 min
280°–282°: 2 h 2 min (0.10 mm)
282°–325°: 4 min (0.10 mm)
325°–328°: 17 min (0.10 mm)
The product was isolated, ground up in a micro mill to pass through a 20 mesh screen (U.S. Sieve Series) and dried in a vacuum oven at 200° for about 17 h; 26.3 g of polymer was obtained having an inherent viscosity of 1.80. This polyester formed an anisotropic melt above its flow temperature of 207°.

Melt-spinning of this polyester at 268°–312° gave lustrous filament. Filament collected at 312° had the following properties:
Tensile Strength: 3.65 g/denier
% Elongation: 1.31%
Initial Modulus: 330 g/denier C. Copolyester of Phenylterephthalic Acid, 2,6-Dihydroxynaphthalene, and HBA, Containing 3.0 Moles of HBA per Mole of Phenylterephthalic Acid Using the procedure described in Example 1A, a mixture of 17.85 g of 4-acetoxybenzoic acid, 8.00 g of phenylterephthalic acid, an 8.07 g of 2,6-dihydroxynaphthalene diacetate was heated in an oil bath, stirred, and evacuated according to the following schedule:
Oil Bath Temperature
280°: 36 min, stirred 30 min
280°–283°: 1 h 29 min
283°–280°: 2 h (0.10 mm)
280°–330°: 5 min (0.10 mm)
330°–228°: 20 min (0.10 mm)
The product was isolated, ground up in a micro mill to pass through a 40 mesh screen (U.S. Sieve Series), and dried in a vacuum oven at 200° for about 17 h; 20.2 g of polymer was obtained having an inherent viscosity of 3.09. This polyester formed an anisotropic melt above its flow temperature of 251°.

Melt-spinning of this polyester at 317°–328° gave lustrous filament. Filament collected at 317° had the following properties:
Tensile Strength: 4.65 g/denier
% Elongation: 1.60%
Initial Modulus: 320 g/denier
A sample of this filament was heated in a nitrogen atmosphere according to the following schedule:
160°–255°: 6 h
255°: 10 h
255°–160°: 6 h
After this heat treatment, values of tensile strength and initial modulus up to 11.16 g/denier and 453 g/denier, respectively, were obtained.

EXAMPLE 6

A. Copolyester of Phenylterephthalic Acid, Terephthalic Acid, 2,6-Dihydroxynaphthalene, and HBA, Containing 4.0 Moles of HBA and 1.0 Mole of Terephthalic Acid per Mole of Phenylterephthalic Acid Using the procedure described in Example 1A, a mixture of 11.90 g of 4-acetoxybenzoic acid, 4.00 g of phenylterephthalic acid, 2.74 g of terephthalic acid, and 8.47 g of 2,6-dihydroxynaphthalene diacetate was heated in an oil bath, stirred, and evacuated according to the following schedule:

Oil Bath Temperature
230°–228°: 5 min
228°–222°: 1 h, stirred
222°–280°: 5 min, stirred
280°–284°: 2 h, stirred
284°–300°: 3 min, stirred
300°: 56 min, stirred
300°–325°: 4 min, stirred
325°: 3 min
325°: 15 min (0.10 mm)

The product was isolated, broken up, and dried in a vacuum oven at 150° for about 17 h; 17.8 g of polymer was obtained. Long lustrous filament was manually drawn from this material on a heated metal block over the temperature range of 296° to 367°.

B. Copolyester of Phenylterephthalic Acid, Terephthalic Acid, 4,4'-Dihydroxybiphenyl, and HBA, Containing 0.67 Mole of HBA and 0.33 Mole of Terephthalic Acid per Mole of Phenylterephthalic Acid Using the procedure described in Example 1A, a mixture of 3.97 g of 4-acetoxybenzoic acid, 8.00 g of phenylterephthalic acid, 1.83 g of terephthalic acid, and 12.50 g of 4,4'-dihydroxybiphenyl diacetate was heated in an oil bath, stirred, and evacuated according to the following schedule:

Oil Bath Temperature
230°–225°: 16 min
225°–222°: 42 min, stirred
222°–280°: 5 min, stirred
280°–285°: 2 h 5 min, stirred
285°–300°: 2 min, stirred
300°–303°: 59 min, stirred
303°–325°: 3 min, stirred
325°: 6 min
325°: 30 min (0.15 mm)

The product was isolated, broken up, and dried in a vacuum oven at 150° for about 17 h; 18.5 g of polymer was obtained having an inherent viscosity of 1.65 (0.1% in pentafluorophenol at 60°).

Melt-spinning of this polyester at 290°–315° gave lustrous filament.

EXAMPLE 7

Copolyester of Phenylterephthalic Acid, Chlorohydroquinone, and HBA, Containing 2.0 Moles of HBA per Mole of Phenylterephthalic Acid Using the procedure described in Example 1A, a mixture of 14.87 g of 4-acetoxybenzoic acid, 10.00 g of phenylterephthalic acid, and 10.00 g of chlorohydroquinone diacetate was heated in an oil bath, stirred and evacuated according to the following schedule:

Oil Bath Temperature
280°: 6 min
280°–282°: 31 min, stirred
282°–284°; 1 h 23 min
284°: 2 h 4 min (less than 0.05 mm)
284°–330°: 5 min (less than 0.05 mm)
330°–326°: 17 min (less than 0.05 mm)

The product was isolated, ground up in a micro mill to pass through a 20 mesh screen (U.S. Sieve Series), and dried in a vacuum oven at 200° for about 17 h; 15.7 g of polymer was obtained having an inherent viscosity of 0.65. This polyester formed an anisotropic melt above its flow temperature of 218°. Long lustrous filament was manually drawn from this material on a heated metal block at 235°.

We claim:

1. Fiber forming melt-spinnable polyester that is optically anisotropic in the melt and consists essentially of recurring units having the structural formulas (1) (a) 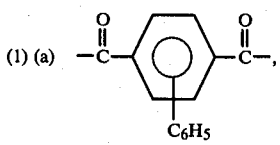

or a combination of (a) and up to 50 mole percent of (b) 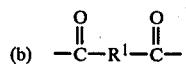

wherein $R^1$ is 1,4-phenylene, 2,6-naphthylene, 4,4'-biphenylene, or a mixture of any thereof;

(2) (a) —O—$R^2$—O—
wherein $R^2$ is 1,4-phenylene, monochloro-, monophenyl-, or monoalkyl-1,4-phenylene wherein alkyl contains 1 to 4 carbon atoms, 2,6-naphthylene, 1,4-naphthylene, 4,4'-biphenylene or a mixture of any thereof, or a combination of (a) and up to 20 mole percent of (b) 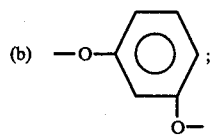

and (3) based on the total moles of (1) and (3), 25 to 80 mole percent of

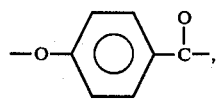

the recurring diacid units (1) and recurring dioxy units (2) being present in substantially equimolar amounts.

2. The polyester of claim 1 consisting essentially of recurring units having the structural formulas

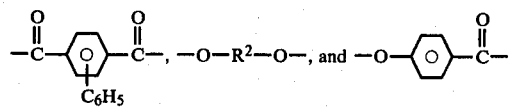

wherein $R^2$ is 1,4-phenylene, monochloro-, monophenyl-, or monoalkyl-1,4-phenylene wherein alkyl contains 1 to 4 carbon atoms, 2,6-naphthylene, 1,4-naphthylene, 4,4'-biphenylene or mixtures thereof.

3. The polyester of claim 2 wherein $R^2$ is 1,4-phenylene.

4. The polyester of claim 1 wherein $R^1$ is 1,4-phenylene.

5. The polyester of claim 4 wherein $R^2$ is 1,4-phenylene.

6. The polyester of claim 1 consisting essentially of units having the structural formulas

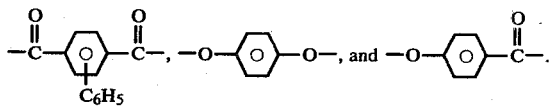

7. The polyester of claim 1 wherein 30 to 70 mole percent of recurring unit (3) is present.

8. The polyester of claim 6 wherein 30 to 70 mole percent of recurring unit (3) is present.

9. Filament of the polyester of claim 1.

* * * * *

UNITED STATES PATENT OFFICE
CERTIFICATE OF CORRECTION

PATENT NO. : 4,391,966
DATED : July 5, 1983
INVENTOR(S) : John Ferguson Harris, Jr.

It is certified that error appears in the above-identified patent and that said Letters Patent are hereby corrected as shown below:

Column 2, line 45 and Column 14, line 50, the formula should read:

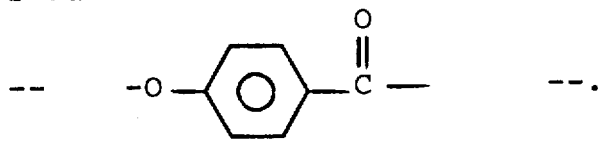

Column 5, line 29, "instead" should be --inserted--.

Signed and Sealed this

Sixth Day of December 1983

[SEAL]

Attest:

GERALD J. MOSSINGHOFF

Attesting Officer     Commissioner of Patents and Trademarks